United States Patent
Lee et al.

(10) Patent No.: US 10,405,769 B2
(45) Date of Patent: Sep. 10, 2019

(54) ELECTRICAL STIMULATION AND BIO-POTENTIAL MEASUREMENT DEVICE

(71) Applicant: Y-BRAIN INC., Daejeon (KR)

(72) Inventors: Ki Won Lee, Daejeon (KR); Cheon Ju Ko, Yongin-si (KR); Jong Min Jang, Suwon-si (KR); Byung Gik Kim, Daegu (KR)

(73) Assignee: Y-BRAIN INC., Daejeon (KR)

(*) Notice: Subject to any disclaimer, the term of this patent is extended or adjusted under 35 U.S.C. 154(b) by 0 days.

(21) Appl. No.: 15/831,764

(22) Filed: Dec. 5, 2017

(65) Prior Publication Data

US 2018/0092565 A1 Apr. 5, 2018

Related U.S. Application Data (63) Continuation of application No. PCT/KR2016/006431, filed on Jun. 17, 2016.

(30) Foreign Application Priority Data

Jun. 23, 2015 (KR) .................. 10-2015-0089220

(51) Int. Cl.
*A61N 1/04* (2006.01)
*A61B 5/04* (2006.01)
(Continued)

(52) U.S. Cl.
CPC ........ *A61B 5/0472* (2013.01); *A61B 5/04004* (2013.01); *A61B 5/0408* (2013.01);
(Continued)

(58) Field of Classification Search
CPC . A61B 5/04004; A61B 5/0472; A61B 5/0408; A61B 5/0476; A61N 1/04; A61N 1/20; A61N 1/36014
See application file for complete search history.

(56) References Cited

U.S. PATENT DOCUMENTS

| | | | | |
|---|---|---|---|---|
| 2011/0193633 | A1* | 8/2011 | Yoon | A61B 5/048 330/260 |
| 2013/0079659 | A1* | 3/2013 | Akhadov | A61B 5/0476 600/544 |
| 2015/0141529 | A1 | 5/2015 | Hargrove | |

FOREIGN PATENT DOCUMENTS

| | | |
|---|---|---|
| KR | 10-2015-0061609 A | 6/2015 |
| KR | 10-2015-0062905 A | 6/2015 |
| KR | 10-1566786 B1 | 11/2015 |

OTHER PUBLICATIONS

International Search Report issued in PCT/KR2016/006431; dated Sep. 12, 2016.

(Continued)

*Primary Examiner* — Paula J Stice
(74) *Attorney, Agent, or Firm* — Studebaker & Brackett PC (57) ABSTRACT

An electrical stimulation and bio-potential measurement device is provided. The electrical stimulation and bio-potential measurement device comprises at least one electrode module which comes into contact with the scalp of a user, a current supply unit, connected to the at least one electrode module, for supplying a current to the at least one electrode module so that the at least one electrode module can apply electrical stimulation to the user, and a signal processing unit, connected to the at least one electrode module, for processing bio-potential signals detected by the at least one electrode module, wherein the current supply unit comprises at least one switch which is arranged between the at least one electrode module and a voltage source for supplying the current.

8 Claims, 5 Drawing Sheets

(51) Int. Cl.
*A61B 5/0472* (2006.01)
*A61B 5/0476* (2006.01)
*A61N 1/36* (2006.01)
*A61B 5/0408* (2006.01)
*A61N 1/20* (2006.01)
*A61B 5/0478* (2006.01)
*A61B 5/0492* (2006.01)
*A61B 5/0496* (2006.01)
*A61B 5/0448* (2006.01)
*A61B 5/053* (2006.01)

(52) U.S. Cl.
CPC .......... *A61B 5/0476* (2013.01); *A61B 5/0478* (2013.01); *A61B 5/04085* (2013.01); *A61B 5/0492* (2013.01); *A61B 5/0496* (2013.01); *A61N 1/04* (2013.01); *A61N 1/0492* (2013.01); *A61N 1/20* (2013.01); *A61N 1/36* (2013.01); *A61N 1/36014* (2013.01); *A61B 5/0448* (2013.01); *A61B 5/053* (2013.01)

(56) References Cited

OTHER PUBLICATIONS

An Office Action; "Notice of Allowance," issued by the Korean Intellectual Property Office dated Oct. 29, 2015, which corresponds to Korean Patent Application No. 10-2015-0089220.

\* cited by examiner

ELECTRICAL STIMULATION AND BIO-POTENTIAL MEASUREMENT DEVICE

CROSS-REFERENCE TO RELATED APPLICATIONS

The present application is a continuation of International Patent Application No. PCT/KR2016/006431, filed on Jun. 17, 2016, which is based upon and claims the benefit of priority to Korean Patent Application No. 10-2015-0089220, filed on Jun. 23, 2015. The disclosures of the above-listed applications are hereby incorporated by reference herein in their entirety.

BACKGROUND

Embodiments of the inventive concept described herein relate to a medical device, and more particularly, relate to an electrical stimulation and bio-potential measurement device.

It has been known that technology for brain electrical stimulation using transcranial direct current stimulation (tDCS) is effective to increase cognitive abilities and treat mental diseases such as depression and attention deficit hyperactivity disorder (ADHD).

Further, bio-potential measurement technology using electroencephalogram (EEG) has been used to diagnose a variety of cerebropathia, study functions of brains, or measure brain activity.

SUMMARY

Embodiments of the inventive concepts provide an electrical stimulation and bio-potential measurement device which includes at least one electrode module for facilitating both of electrical stimulation and bio-potential measurement.

The technical problems to be solved by the inventive concept are not limited to the aforementioned problems, and any other technical problems not mentioned herein will be clearly understood from the following description by those skilled in the art to which the inventive concept pertains.

According to an aspect of an embodiment, an electrical stimulation and bio-potential measurement device may include at least one electrode module configured to come into contact with a scalp of a user, a current supply unit configured to be connected with the at least one electrode module and supply current to the at least one electrode module such that the at least one electrode module provides electrical stimulation to the user, and a signal processing unit configured to be connected with the at least one electrode module and process a bio-potential signal detected by the at least one electrode module The current supply unit may include at least one switch configured to be located between a voltage source for supplying the current and the at least one electrode module. The at least one switch may be turned on when operated in an electrical stimulation mode and may be turned off when operated in a bio-potential measurement mode.

According to another aspect of an embodiment, an electrical stimulation and bio-potential measurement device may include a plurality of electrode modules configured to include a first electrode module configured to come into contact with a scalp of a user and a second electrode module configured to come into contact with the scalp of the user, a current supply unit configured to be connected with the first electrode module and supply current to the first electrode module such that the first electrode module provides electrical stimulation to the user, and a signal processing unit configured to be connected with the first electrode module and the second electrode module and process a bio-potential signal detected by each of the first electrode module and the second electrode module. The current supply unit may include at least one switch configured to be located between a voltage source for supplying the current and the first electrode module. The at least one switch may be turned on when operated in an electrical stimulation mode and may be turned off when operated in a bio-potential measurement mode.

According to another aspect of an embodiment, an electrical stimulation and bio-potential measurement device may include a plurality of electrode modules configured to include a first electrode module configured to come into contact with a scalp of a user, a second electrode module configured to come into contact with the scalp of the user, and a third electrode module configured to come into contact with the scalp of the user, a current supply unit configured to be connected with the first electrode module and supply current to the first electrode module such that the first electrode module provides electrical stimulation to the user, and a signal processing unit configured to be connected with the first electrode module, the second electrode module, and the third electrode module and process a bio-potential signal detected by each of the first electrode module, the second electrode module, and the third electrode module. The first electrode module may be a module for electrical stimulation and bio-potential measurement. The second electrode module may be a module for bio-potential measurement. The third electrode module may be a module for bio-potential readout. The current supply unit may include at least one switch configured to be located between a voltage source for supplying the current and the first electrode module. The at least one switch may be turned on when operated in an electrical stimulation mode and may be turned off when operated in a bio-potential measurement mode.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

The above and other aspects, features and advantages of the invention will become apparent from the following description of the following embodiments given in conjunction with the accompanying drawings. However, the inventive concept is not limited to the embodiments disclosed below, but may be implemented in various forms. The embodiments of the inventive concept are provided to make the disclosure of the inventive concept complete and fully inform those skilled in the art to which the inventive concept pertains of the scope of the inventive concept.

The terms used herein are provided to describe the embodiments but not to limit the inventive concept. In the specification, the singular forms include plural forms unless particularly mentioned. The terms "comprises" and/or "comprising" used herein does not exclude presence or addition of one or more other elements, in addition to the aforementioned elements. Throughout the specification, the same reference numerals dente the same elements, and "and/or" includes the respective elements and all combinations of the elements. Although "first", "second" and the like are used to describe various elements, the elements are not limited by the terms. The terms are used simply to distinguish one element from other elements. Accordingly, it is apparent that a first element mentioned in the following may be a second element without departing from the spirit of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein.

The term "electrical stimulation" described hereafter indicates transcranial current stimulation (tCS), such as transcranial direct current stimulation (tDCS), transcranial alternating current stimulation (tACS), or transcranial random-noise stimulation (tRNS). However, embodiments of the inventive concept are not limited thereto.

Further, the term "bio-potential measurement" described hereafter may indicate electroencephalogram (EEG), electrocardiogram (ECG), electromyogram (EMG), electrooculography (EOG), or the like. However, embodiments of the inventive concept are not limited thereto.

Hereinafter, a description will be given of an example of an electrical stimulation and bio-potential measurement device using tDCS and EEG according to an exemplary embodiment of the inventive concept.

Figure 1:
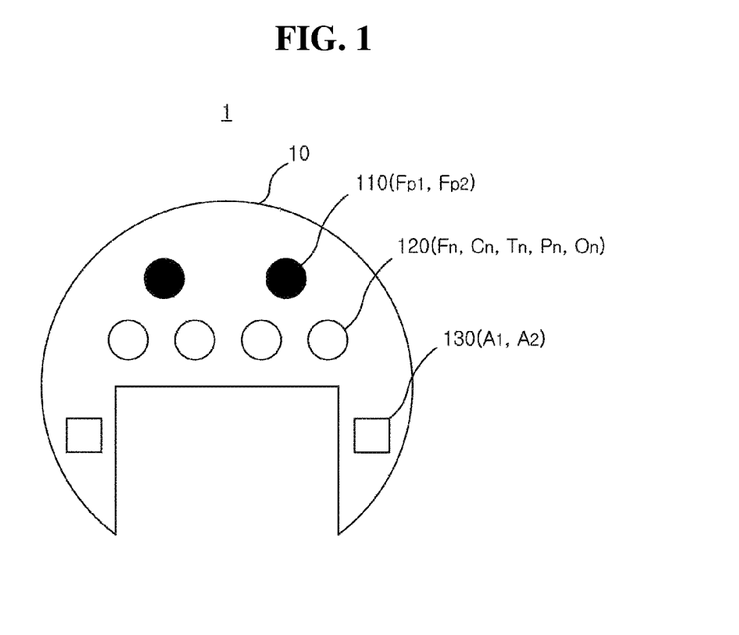
FIGS. 1 and 2 are drawings illustrating a schematic configuration of an electrical stimulation and bio-potential measurement device according to an embodiment of the inventive concept.
Figure 2:
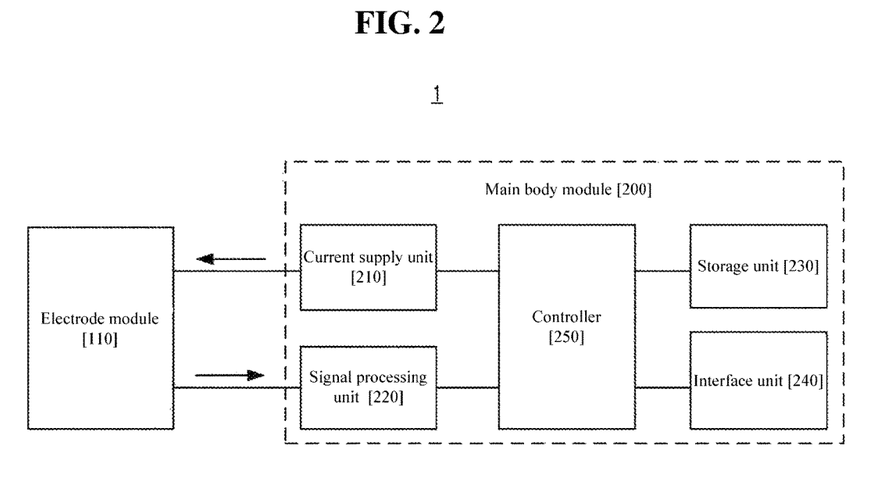

FIGS. 1 and 2 are drawings illustrating a schematic configuration of an electrical stimulation and bio-potential measurement device according to an embodiment of the inventive concept.

Referring to FIGS. 1 and 2, an electrical stimulation and bio-potential measurement device 1 according to an embodiment of the inventive concept may include a plurality of electrode modules 110, 120, and 130 and a main body module 200.

The plurality of electrode modules 110, 120, and 130 may be located on a surface of a main body 10, may be located in the main body 10, or may be connected with the main body 10. As shown in FIG. 1, the main body 10 may be configured in the form of a helmet wearable on a head of a user. However, embodiments of the inventive concept are not limited thereto. The main body 10 may be configured in the form of being attachable to the head of the user. If the user wears or attach to his or her head, the plurality of electrode modules 110, 120, and 130 may come into contact with a scalp (or another body) of the user.

The first electrode module 110 among the plurality of electrode modules 110, 120, and 130 may be a module for electrical stimulation and bio-potential measurement. The second electrode module 120 among the plurality of electrode modules 110, 120, and 130 may be a module for bio-potential measurement. The third electrode module 130 among the plurality of electrode modules 110, 120, and 130 may be a module for bio-potential readout. The module for electrical stimulation may receive current from the main body module 200 and may provide electrical stimulation to the user. The module for bio-potential measurement may detect a bio-potential signal from the user and may transmit the detected bio-potential signal to the main body module 200. The module for bio-potential readout may be used to read the bio-potential signal detected by the module for bio-potential measurement. For example, two modules for bio-potential readout may be provided. One of the two modules for bio-potential readout may provide a ground voltage for detecting a bio-potential signal, and a voltage of a bio-potential signal detected by the other module for bio-potential readout may be used as a reference voltage for reading a bio-potential signal detected by the module for bio-potential measurement.

The first electrode module 110 may supply current and detect current to be different from the second and third electrode modules 120 and 130. Although the first electrode module 110 is a single electrode module, it may be used for electrical stimulation and for bio-potential measurement. The first electrode module 110 may be provided with two or more electrode modules.

A plurality of electrode modules 110, 120, and 130 may be located to be spaced apart from each other depending on an operation region (or portion). For example, the first electrode module 110 may be located on a ventromedial prefrontal cortex region, and the second electrode module 120 may be located on a dorsolateral prefrontal cortex region, a central lobe region, a temporal lobe region, a parietal lobe region, or an occipital lobe region. The third electrode module 130 may be located on an earlobe region. The above example of classifying the regions and locating the electrode modules complies with the "International 10-20 system". Embodiments of the inventive concept are not limited thereto.

Figure 3:
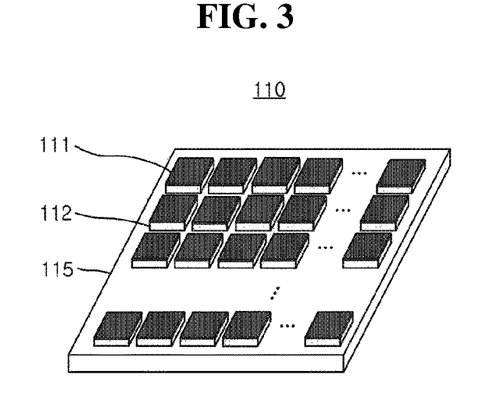
FIG. 3 is a drawing schematically illustrating a detailed configuration of an electrode module of FIG. 1.

FIG. 3 is a drawing schematically illustrating a detailed configuration of an electrode module of FIG. 1.

Referring to FIG. 3, a first electrode module 110 may include a patch layer 111 and an electrode layer 112.

The patch layer 111 may come into direct contact with a scalp of a user. The patch layer 111 may be configured as a single layer. The patch layer 111 may provide electrical stimulation to a head of the user using current transmitted from the electrode layer 112. For this purpose, the patch layer 111 may include an electrolyte for transmitting current. For example, the patch layer 111 may be configured with a sponge or hydrogel including the electrolyte. However, embodiments of the inventive concept are limited thereto. The electrolyte may include chlorine ion (Cl—) which is in common with a skin of the user. The patch layer 111 may be formed of material with relatively high impedance.

The electrode layer 112 may fail to come into contact with the scalp of the user. The electrode layer 112 may transmit current to the patch layer 111 to provide electrical stimulation to the user through the patch layer 111. For example, the electrode layer 112 may be configured with a conductive carbon sheet or conductive silicon. Embodiments of the inventive concept are not limited thereto.

In an embodiment of the inventive concept, the first electrode module 110 may include a plurality of segments. The plurality of segments may be spaced apart from each other to be formed on the same base 115. Each of the plurality of segments may include the patch layer 111 and the electrode layer 112. The number of the plurality of segments, a shape of each of the plurality of segments, or an interval between the plurality of segments may vary in various manners according to an embodiment. The plurality of segments may be controlled to be independent of each other. Alternatively, some of the plurality of segments may be grouped and controlled.

Each of a second electrode 120 and a third electrode 130 may be a module for measurement, and a dry electrode configured by coating Au, Ag, Ag/AgCl, and the like on a conducting polymer may be mainly used as each of the second electrode 120 and the third electrode 130. However, embodiments of the inventive concept are not limited thereto.

A main body module 200 may be located on a surface (or an upper or front surface) of a main body 10 or may be located in the main body 10. The main body module 200 may control the plurality of electrode modules 110, 120, and 130 to operate the plurality of electrode modules 110, 120, and 130. FIG. 2 is a drawing illustrating the gist of the inventive concept. FIG. 2 illustrates only a connection between the first electrode module 110 and the main body module 200 and does not clearly illustrate the other electrode modules 120 and 130. However, it may be apparent to those skilled in the art that the other electrode modules 120 and 130 are connected with the main body module 200 to be controlled.

The main body module 200 may include a current supply unit 210, a signal processing unit 220, a storage unit 230, an interface unit 240, and a controller 250 which are detailed elements.

The current supply unit 210 may be connected with the first electrode module 110 and may supply current to the first electrode module 110 such that the first electrode module 110 provides electrical stimulation to the user.

Figure 4:
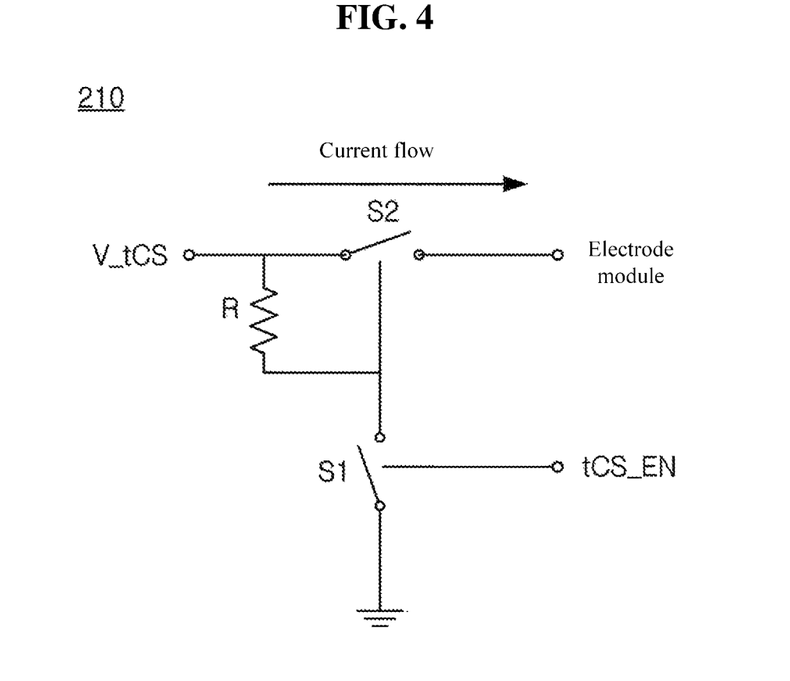
FIG. 4 is a drawing schematically illustrating a detailed configuration of a current supply unit of FIG. 2.

FIG. 4 is a drawing schematically illustrating a detailed configuration of a current supply unit of FIG. 2.

Referring to FIG. 4, a current supply unit 210 may include a switch located between a voltage source V_tCS for supplying current for electrical stimulation and a first electrode module 110. Only when the switch is turned on, current for electrical stimulation may be supplied from the voltage source V_tCS to the first electrode module 110.

In an embodiment of the inventive concept, the current supply unit 210 may include two switches S1 and S2. The first switch Si may be turned off according to an electrical stimulation enable signal tCS_EN. For example, the first switch S1 may be turned on when the electrical stimulation enable signal tCS_EN has a first level (high level) and may be turned off when the electrical stimulation enable signal tCS_EN has a second level (low level). The second switch S2 may be located between the voltage source V_tCS and the first electrode module 110 and may be turned off according to whether the first switch S1 is turned on (that is, whether the first switch S1 is connected with the ground). For example, if the first switch S1 is turned on to be connected with the ground, the second switch S2 may be turned on. If the first switch Si is not turned on not to be connected with the ground, the second switch S2 may be turned off. A pull-up resistor R may be located between the voltage source V_tCS and the first switch S1. The current supply unit 210 may further include a voltage booster circuit and a constant current circuit (e.g., a current regulator diode (CRD) or the like).

The signal processing unit 220 may be connected with the first electrode module 110 and may receive a bio-potential signal detected by the first electrode module 110, thus processing the received bio-potential signal. Although not clearly shown, as described above, the signal processing unit 220 may be connected with the other electrode modules 120 and 130.

Figure 5:
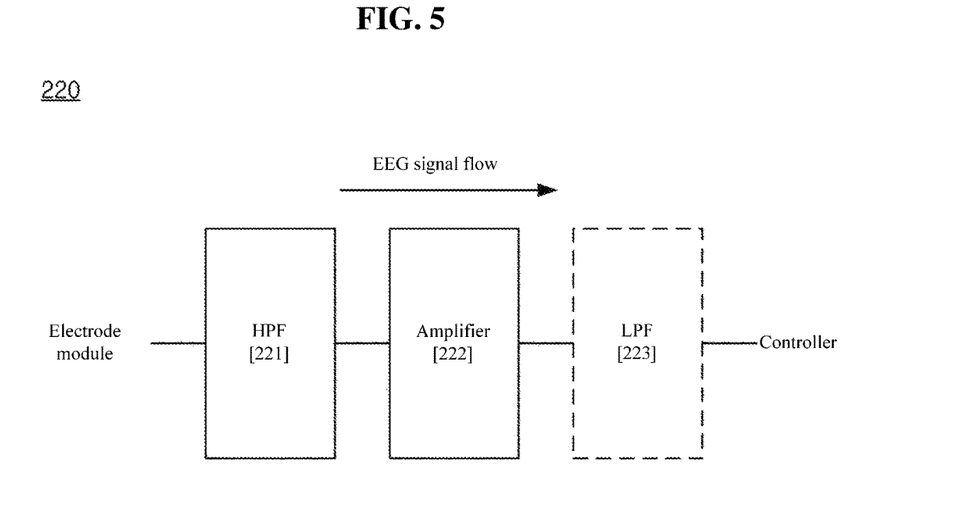
FIG. 5 is a drawing schematically illustrating a detailed configuration of a signal processing unit of FIG. 2.

FIG. 5 is a drawing schematically illustrating a detailed configuration of a signal processing unit of FIG. 2.

Referring to FIG. 5, a signal processing unit 220 may include a high pass filter (HPF) 221 for filtering an EEG signal received from a first electrode module 110 and an amplifier 222 for amplifying the signal filtered by the HPF 221. Elements of the main body module 200 may be prevented from being damaged as part of current for electrical stimulation unintentionally flows to a main body module 200 in an electrical stimulation mode by providing the HPF 221. Further, the HPF 221 may remove a DC component from a bio-potential signal detected by the first electrode module 110.

According to an embodiment, the signal processing unit 220 may further include a low pass filter (LPF) 223 for filtering the signal amplified by the amplifier 222. The HPF 221, the amplifier 222, and the LPF 223 may be employed to obtain a signal of a desired frequency domain. However, embodiments of the inventive concept are not limited thereto. The signal processing unit may include one or more filters and/or one or more amplifiers.

A storage unit 230 may store a command and program for an operation of an electrical stimulation and bio-potential measurement device 1, protocol data for electrical stimulation, data and an algorithm for bio-potential readout, or a variety of other information. The storage unit 230 may be configured as a random access memory (RAM), a read only memory (ROM), an erasable programmable ROM (EPROM), an electrically EPROM (EEPROM), a flash memory, or the like.

An interface unit 240 may interface with a user. The interface unit 240 may receive a variety of information from the user and may output a variety of information to the user. For this purpose, the interface unit 240 may include an input means such as a keypad, a button, a switch, a touch pad, or a jog wheel. If the touch pad and a display module described below are configured with a layer structure, they may be configured as a touch screen. The interface unit 240 may include an output means such as a display module, a speaker module, or a haptic module. The display module may be provided in any form, for example, a plasma display panel (PDP), a liquid crystal display (LCD), a thin film transistor LCD (TFT LCD), an organic light emitting diode (OLED), a flexible display, a three-dimensional (3D) display, or an electronic-link (e-link) display.

A controller 250 may control an overall operation of the electrical stimulation and bio-potential measurement device 1. For example, the controller 250 may be configured as a processor, a microprocessor, a microcontroller, a central processing unit (CPU), a micro processing unit (MPU), a micro controlling unit (MCU), or the like. Firmware for performing a control operation may be provided in the controller 250.

The controller 250 may receive an input of the user through the interface 240 and may determine an operation of the electrical stimulation and bio-potential measurement device 1 or may change an operation mode. The controller 250 may generate an electrical stimulation enable signal tCS_EN of a first level (a high level) upon an electrical stimulation mode and may generate the electrical stimulation enable signal tCS_EN of a second level (a low level) upon an EEG measurement mode, thus controlling an operation of the current supply unit 210. The controller 250 may read bio-potential of the user using data and an algorithm stored in the storage unit 230. The controller 250 may generate a command (or signal) for providing electrical stimulation depending on protocol data for electrical stimulation, stored in the storage unit 230, and/or the read result.

Although not clearly shown, a main body module 200 may further include a power supply unit. The power supply unit may include a battery and may supply power for operating the current supply unit 210, the signal processing unit 220, the storage unit 230, the interface unit 240, or the controller 250.

Since the elements shown in FIGS. 1 and 2 are not essential elements of the electrical stimulation and bio-potential measurement device 1 according to an embodiment of the inventive concept, the electrical stimulation and bio-potential measurement device 1 may be configured as a device including more elements (e.g., a wired/wireless communication unit and various sensors such as a geomagnetic sensor, a gyro sensor, and an acceleration sensor) than the elements shown in FIGS. 1 and 2 or including less elements than the elements shown in FIGS. 1 and 2.

In the specification, an embodiment is exemplified as the device 1 for providing electrical stimulation to a head of the user or measuring a bio-potential signal from the head of the user. However, it may be apparent to those skilled in the art that technical features of the inventive concept are applied to be substantially the same as another type of device for providing electrical stimulation to another body portion of the user except for the head of the user or measuring a bio-potential signal.

An electrical stimulation and bio-potential measurement device according to an embodiment of the inventive concept may facilitate both of electrical stimulation and bio-potential measurement using a single electrode module.

Further, the electrical stimulation and bio-potential measurement device may facilitate a valid remedy by real-time control by simultaneously or consecutively performing electrical stimulation and bio-potential measurement.

Further, the electrical stimulation and bio-potential measurement device may provide user convenience by facilitating both of electrical stimulation and bio-potential measurement.

Effects of the inventive concept are not limited to the above-mentioned effects, and other effects not described above may be clearly understood to those skilled in the art from the description below.

Although the exemplary embodiments of the inventive concept have been described with reference to the accompanying drawings, it will be understood by those skilled in the art to which the inventive concept pertains that the inventive concept can be carried out in other detailed forms without changing the technical spirits and essential features thereof. Therefore, the above-described embodiments are exemplary in all aspects, and should be construed not to be restrictive.

What is claimed is:

1. An electrical stimulation and bio-potential measurement device, the device comprising:
   a plurality of electrode modules including a first electrode module including at least one electrode configured to come into contact with a scalp of a user when the device is worn by the user, and a second electrode module including at least one electrode configured to come into contact with the scalp of the user when the device is worn by the user;
   a current supplier connected with the first electrode module and configured to supply current to the first electrode module such that the first electrode module provides electrical stimulation to the user; and
   a signal processor connected with the first electrode module and the second electrode module, and configured to process a bio-potential signal detected by each of the first electrode module and the second electrode module,
   wherein the current supplier comprises:
   at least one switch located between a voltage source for supplying the current and the first electrode module, and
   wherein the at least one switch is configured to be turned on when operated in an electrical stimulation mode and turned off when operated in a bio-potential measurement mode, and
   wherein, when the at least one switch is turned on, the first electrode module is configured to provide electrical stimulation to the user and not to detect the bio-potential signal from the user, and the second electrode module is configured to detect the bio-potential signal from the user.

2. The device of claim 1, wherein the at least one switch comprises:
   a first switch configured to be turned on or off according to an electrical stimulation enable signal;
   a second switch configured to be located between the voltage source and the first electrode module and be turned on or off as the first switch is turned on; and
   a resistor configured to be located between the voltage source and the first switch.

3. The device of claim 1, wherein the signal processing unit comprises:
   at least one high pass filter (HPF) configured to filter the bio-potential signal received from at least one of the first electrode module and the second electrode module.

4. The device of claim 1, wherein the signal processing unit further comprises:
   at least one amplifier configured to amplify the signal filtered by the at least one HPF.

5. The device of claim 4, wherein the signal processing unit further comprises:
   at least one low pass filter (LPF) configured to filter the signal amplified by the at least one amplifier.

6. The device of claim 1, wherein the electrical stimulation comprises at least one of transcranial direct current stimulation (tDCS), transcranial alternating current stimulation (tACS), or transcranial random-noise stimulation (tRNS).

7. The device of claim 1, wherein the bio-potential signal comprises at least one of electroencephalogram (EEG), electrocardiogram (ECG), electromyogram (EMG), or electrooculography (EOG).

8. An electrical stimulation and bio-potential measurement device, the device comprising:
   a plurality of electrode modules including a first electrode module including at least one electrode configured to come into contact with a scalp of a user when the device is worn by the user, a second electrode module including at least one electrode configured to come into contact with the scalp of the user when the device is worn by the user, and a third electrode module including at least one electrode configured to come into contact with the scalp of the user when the device is worn by the user;
   a current supplier connected with the first electrode module and configured to supply current to the first electrode module such that the first electrode module provides electrical stimulation to the user; and a signal processor connected with the first electrode module, the second electrode module, and the third electrode module, and configured to process a bio-potential signal detected by each of the first electrode module, the second electrode module, and the third electrode module, wherein the first electrode module is a module for electrical stimulation and bio-potential measurement, wherein the second electrode module is a module for bio-potential measurement, wherein the third electrode module is a module for bio-potential readout, wherein the current supplier comprises:

at least one switch located between a voltage source for supplying the current and the first electrode module, and wherein the at least one switch is configured to be turned on when operated in an electrical stimulation mode and turned off when operated in a bio-potential measurement mode, and wherein, when the at least one switch is turned on, the first electrode module is configured to provide electrical stimulation to the user and not to detect the bio-potential signal from the user, the second electrode module is configured to detect the bio-potential signal from the user, and the third electrode module is configured to provide a ground voltage for detecting the bio-potential signal and a reference voltage for reading a detected bio-potential signal.

* * * * *